US009522116B2

(12) United States Patent
Epstehin

(10) Patent No.: US 9,522,116 B2
(45) Date of Patent: *Dec. 20, 2016

(54) SOLID ORAL FORM OF A MEDICINAL PREPARATION AND A METHOD FOR THE PRODUCTION THEREOF

(75) Inventor: Oleg Iliich Epstehin, Moscow (RU)

(73) Assignee: Oleg Iliich Epshtein, Moscow (RU)

( * ) Notice: Subject to any disclaimer, the term of this patent is extended or adjusted under 35 U.S.C. 154(b) by 648 days.

This patent is subject to a terminal disclaimer.

(21) Appl. No.: 12/282,614

(22) PCT Filed: May 16, 2006

(86) PCT No.: PCT/RU2006/000237
§ 371 (c)(1),
(2), (4) Date: Feb. 23, 2009

(87) PCT Pub. No.: WO2007/105981
PCT Pub. Date: Sep. 20, 2007

(65) Prior Publication Data
US 2009/0148521 A1    Jun. 11, 2009

(30) Foreign Application Priority Data

Mar. 13, 2006    (RU) ................ 2006107580

(51) Int. Cl.
*A61K 39/395* (2006.01)
*A61K 9/20* (2006.01)
*A61K 41/00* (2006.01)

(52) U.S. Cl.
CPC ....... *A61K 9/2018* (2013.01); *A61K 39/39591* (2013.01); *A61K 41/0004* (2013.01)

(58) Field of Classification Search
None
See application file for complete search history.

(56) References Cited

U.S. PATENT DOCUMENTS

| | | | |
|---|---|---|---|
| 3,901,967 A | | 8/1975 | Cohen et al. |
| 4,963,367 A | | 10/1990 | Ecanow |
| 5,006,491 A | | 4/1991 | Ueda et al. |
| 5,066,491 A | * | 11/1991 | Stott et al. ........... 424/157.1 |
| 5,244,663 A | | 9/1993 | Bruttmann et al. |
| 5,629,286 A | | 5/1997 | Brewitt |
| 5,683,712 A | | 11/1997 | Cavazza |
| 5,698,195 A | | 12/1997 | Le et al. |
| 5,741,488 A | | 4/1998 | Feldman et al. |
| 5,780,028 A | | 7/1998 | Graham |
| 5,846,514 A | | 12/1998 | Foster et al. |
| 5,879,677 A | | 3/1999 | del Zoppo |
| 6,187,803 B1 | * | 2/2001 | Yoshii et al. ........... 514/400 |
| 6,248,355 B1 | | 6/2001 | Seth |
| 6,294,197 B1 | | 9/2001 | Wagner et al. |
| 6,326,360 B1 | | 12/2001 | Kanazawa et al. |
| 7,572,441 B2 | | 8/2009 | Epshtein et al. |
| 7,582,294 B2 | | 9/2009 | Epshtein et al. |
| 7,700,096 B2 | | 4/2010 | Epshtein et al. |
| 7,815,904 B2 | | 10/2010 | Epshtein et al. |
| 7,923,009 B2 | | 4/2011 | Epshtein et al. |
| 8,066,992 B2 | | 11/2011 | Epshtein |
| 8,168,182 B2 | | 5/2012 | Epshtein |
| 8,178,498 B1 | | 5/2012 | Ephstein |
| 8,241,625 B2 | | 8/2012 | Epshtein et al. |
| 8,524,229 B2 | | 9/2013 | Epshtein et al. |
| 8,535,664 B2 | | 9/2013 | Epshtein et al. |
| 8,617,555 B2 | | 12/2013 | Epshtein |
| 8,637,030 B2 | | 1/2014 | Epshtein |
| 8,637,034 B2 | | 1/2014 | Epshtein |
| 8,703,124 B2 | | 4/2014 | Epshtein et al. |
| 8,795,657 B2 | | 8/2014 | Epshtein |
| 8,815,245 B2 | | 8/2014 | Epshtein |

(Continued)

FOREIGN PATENT DOCUMENTS

CA    2654408 A1    12/2007
EP    0687466 A1    12/1995

(Continued)

OTHER PUBLICATIONS

International Search Report from International Application No. PCT/RU04/000374, filed Sep. 27, 2004, mailed on Feb. 10, 2005.
Pavlov et al., "Behavoral Effects of Potentiated Morphine Forms," Bull of Siberan Branch of RAMS No 1 (91), 1999.
Beregovoy et al., On influence of various Dilutions of Monoclonal Antibodies 5F5-B6 on the Formation of Long-Term Post-Tetanic Potentiation in Survived Hippocampal Slices, Bull of Siberian Branch of RAMS No. 1 (91), 1999.
Shang et al., 2005, Lancet, vol. 366: 726-32.
Linde et al., 1997, Lancet, vol. 350: 834-43.
Davenas et al., Nature, 1988, 333: 816-818.

(Continued)

*Primary Examiner* — Yunsoo Kim
(74) *Attorney, Agent, or Firm* — Pergament & Cepeda LLP; Milagros A. Cepeda; Edward D. Pergament

(57) ABSTRACT

A solid oral form of an antibody-based medicinal preparation comprises an effective carrier quantity irrigated with an active form of an antibody aqueous-alcoholic dilution, which is prepared by combining a repeated successive antibody dilution with an external action, and pharmaceutically acceptable additives. The inventive method for producing a solid oral form of the antibody-based medicinal preparation consists in preparing an aqueous-alcoholic dilution of anti-substance antibodies, obtaining the active form by combining a repeated successive dilution and an external action according to a homeopathic process, irrigating a carrier with the thus obtained aqueous-alcoholic dilution in a fluidized boiling bed with concurrent drying of said carrier at a temperature equal to or less than 35° C., mixing in a pharmaceutically acceptable sequence with pharmaceutically acceptable additives and in subsequent pelletization—forming tablets by means of a direct dry pressing.

4 Claims, No Drawings

(56) References Cited

U.S. PATENT DOCUMENTS

| | | |
|---|---|---|
| 2003/0099636 A1 | 5/2003 | Epshtein et al. |
| 2005/0266007 A1 | 12/2005 | Epshtein et al. |
| 2006/0024307 A1 | 2/2006 | Epshteni et al. |
| 2006/0153845 A1 | 7/2006 | Epshtein et al. |
| 2006/0165697 A1 | 7/2006 | Epshtein et al. |
| 2007/0123518 A1 | 5/2007 | Epshtein |
| 2007/0141058 A1 | 6/2007 | Iliich et al. |
| 2008/0025985 A1 | 1/2008 | Iliich et al. |
| 2008/0050360 A1 | 2/2008 | Iliich et al. |
| 2008/0050392 A1 | 2/2008 | Iliich et al. |
| 2008/0131440 A1 | 6/2008 | Epshtein et al. |
| 2009/0148521 A1 | 6/2009 | Epstehin |
| 2010/0166762 A1 | 7/2010 | Epshtein |
| 2010/0203059 A1 | 8/2010 | Epshtein |
| 2010/0221258 A1 | 9/2010 | Epshtein |
| 2010/0239569 A1 | 9/2010 | Epshtein |
| 2011/0008452 A1 | 1/2011 | Epshtein et al. |
| 2011/0086037 A1 | 4/2011 | Iliich |
| 2012/0225074 A1 | 9/2012 | Epshtein et al. |
| 2012/0258146 A1 | 10/2012 | Epshtein |
| 2012/0263725 A1 | 10/2012 | Epshtein et al. |
| 2012/0263726 A1 | 10/2012 | Epshtein et al. |
| 2012/0294899 A1 | 11/2012 | Epshtein et al. |
| 2012/0321672 A1 | 12/2012 | Epshtein |
| 2013/0017202 A1 | 1/2013 | Epshtein et al. |
| 2013/0045237 A1 | 2/2013 | Epshtein et al. |
| 2013/0058981 A1 | 3/2013 | Epshtein |
| 2013/0058982 A1 | 3/2013 | Epshtein |
| 2013/0064860 A1 | 3/2013 | Epshtein |
| 2013/0171161 A1 | 7/2013 | Epshtein et al. |
| 2013/0189707 A1 | 7/2013 | Sergeeva et al. |
| 2013/0224219 A1 | 8/2013 | Epshtein et al. |
| 2013/0302312 A1 | 11/2013 | Epshtein et al. |
| 2013/0303735 A1 | 11/2013 | Epshtein et al. |
| 2013/0315964 A1 | 11/2013 | Epshtein et al. |
| 2013/0336985 A1 | 12/2013 | Epshtein et al. |
| 2014/0010819 A1 | 1/2014 | Epshtein et al. |
| 2014/0056923 A9 | 2/2014 | Epshtein et al. |
| 2014/0112934 A1 | 4/2014 | Epshtein |

FOREIGN PATENT DOCUMENTS

| | | |
|---|---|---|
| EP | 1295606 A1 | 3/2003 |
| EP | 1340493 A1 | 9/2003 |
| JP | 61176534 A | 8/1986 |
| JP | 63270630 A | 11/1988 |
| JP | 9503754 A | 4/1997 |
| JP | 2000512270 A | 9/2000 |
| JP | 2000302691 A | 10/2000 |
| RU | 1836083 A3 | 8/1993 |
| RU | 2007989 C1 | 2/1994 |
| RU | 2033784 C1 | 4/1995 |
| RU | 2035167 C1 | 5/1995 |
| RU | EP0884042 A1 | 8/1997 |
| RU | WO/98/14161 A1 | 4/1998 |
| RU | WO/98/14162 A1 | 4/1998 |
| RU | WO/98/14166 A1 | 4/1998 |
| RU | WO/98/33493 A1 | 8/1998 |
| RU | WO/98/35680 A1 | 8/1998 |
| RU | 2122858 C1 | 12/1998 |
| RU | 2133123 C1 | 7/1999 |
| RU | 98109384 A | 3/2000 |
| RU | 2161481 C2 | 1/2001 |
| RU | WO/01/05371 A1 | 1/2001 |
| RU | 2182008 C1 | 5/2002 |
| RU | 2182492 C1 | 5/2002 |
| RU | 2191601 CI | 10/2002 |
| RU | 2192882 C1 | 11/2002 |
| RU | 2201254 C1 | 3/2003 |
| RU | 2203054 C2 | 4/2003 |
| RU | WO/03/037372 A1 | 5/2003 |
| RU | 2209083 C1 | 7/2003 |
| RU | WO/03/055518 A1 | 7/2003 |
| RU | WO/03/055519 A1 | 7/2003 |
| RU | WO/03/077946 A1 | 9/2003 |
| RU | WO/2004/012765 A1 | 2/2004 |
| RU | WO/2008/097132 A1 | 8/2008 |
| RU | WO/2008/097133 A1 | 8/2008 |
| WO | 9422846 A1 | 10/1994 |
| WO | 9520978 A1 | 8/1995 |
| WO | 9744047 A1 | 11/1997 |
| WO | 9921582 A2 | 5/1999 |
| WO | 0032189 | 6/2000 |
| WO | 2004080381 A2 | 9/2004 |
| WO | 2007105981 A1 | 9/2007 |

OTHER PUBLICATIONS

Janeway et al. Immunobiology, 1997, 3rd edition, Garland Publishing Inc., pp. 3:1-3:11.
Schwab, V., "Homeopathic Pharmaceutical Agents. A manual on description and preparation," Moscow, 1967, pp. 12-38.
International Search Report from International Application No. PCT/RU97/00026, filed Feb. 10, 1997, mailed on Apr. 8, 1997.
Schwabe, W., "German Homeopathic pharmacopoeia (Homeopathisches Arzneibuch)," Stuttgart, Translation of the 5th Supplement (1991) to the 1978 edition.
International Search Report from International Application No. PCT/RU01/00239, filed Jun. 19, 2001, mailed on Sep. 20, 2001.
International Search Report from International Application No. PCT/RU02/00368, filed Aug. 2, 2002, mailed on Dec. 5, 2002.
International Search Report from International Application No. PCT/RU02/00367, filed Aug. 2, 2002, mailed on Dec. 19, 2002.
International Search Report from International Application No. PCT/RU02/00369, filed Aug. 2, 2002, mailed on Dec. 26, 2002.
International Search Report from International Application No. PCT/RU02/00365, filed Aug. 2, 2002, mailed on Dec. 5, 2002.
International Search Report from International Application No. PCT/RU2006/000237,filed May 16, 2006, mailed on Nov. 23, 2006.
English translation of Abstract of Foreign Patent Document EP1340493, 2003.
Thomson Innovation Record English translation of Abstract of Foreign Patent Document JP61176534, 1986.
Notice of Decision for Rejection dated Sep. 10, 2013, issued by the Japanese Patent Office for corresponding Japanese Patent Application No. 2009-500312.
Communication Pursuant to Article 94(3) EPC, dated Mar. 24, 2014, issued by the European Patent Office for corresponding European Patent Application No. 06799634.8-1403.
Notice of Allowance, dated May 7, 2014, issued by the Japanese Patent Office for corresponding Japanese Patent Application No. 2009-500312.
Myagkova, M. A., et al., "Antibodies to Delta Sleep-Inducing Peptide in Ultralow Doses: Study of the Effect by Enzyme Immunoassay," Bull Exp Biol Med., 2003, vol. 135, Suppl. 7, pp. 102-104.
Abecassis J., et al., "2-1/2-2", In: Negtien G, et al., "Medicaments Homeopatiques," 1986, Medicaments Homeopathiques. Notions Pratiques De Pharmacie Homeopatique [Galenica], Paris, Technique et Documentation, FR, XP002162252, pp. 77-99.
Frimel, "Immunological Methods", 1987, Medicina, Moscow, p. 9-33.
Register of Pharmaceuticals of Russia, Encyclopedia of Pharmaceuticals (in Russian), Moscow, 2000, pp. 358-359.
Epshtein, O. I., et al., "Effect of Potentiated Antibodies to Brain-Specific Protein S100 on the Integrative Activity of the Brain," Bull Exp Biol Med, 1999, vol. 127, No. 5, pp. 493-495.
Goldacre, "Benefits and Risks of Homoeopathy," The Lancet, Nov. 17, 2007, vol. 370, pp. 1672-1673.

\* cited by examiner

SOLID ORAL FORM OF A MEDICINAL PREPARATION AND A METHOD FOR THE PRODUCTION THEREOF

FIELD OF INVENTION

The invention relates to the field of medicine and can be used for technologically simple production of the solid oral form of an antibody-based drug for effective treatment of pathological syndrome without pronounced side effects.

PRIOR ART

From prior art, antibody-based drugs are known (sera, immunoglobulins), which are used in therapeutic doses (for example, see Russian Drug Register (in Rus.), Drug Encyclopedia, 7th Ed., 2000, pp.358-359). However, these drugs are prepared in liquid formulation suitable for injections and are introduced parenterally, since this is the only method of introduction providing bioavailability of these drugs.

In addition, the field of application of these drugs is limited to etiological treatment of predominantly infectious diseases; their usage could be associated with adverse side effects.

A method is also known for producing a solid form of a drug, which includes pressing of dry ground components containing active substance and pharmaceutically acceptable additives (RU 2203054 C2, A61K9/20, 2003).

DISCLOSURE OF INVENTION

The invention is aimed at the development of a solid form of an antibody-based drug suitable for oral administration, and a technologically simple method for producing such antibody-based drug in activated form, prepared using homeopathic technique in the form of tablets.

Solution of the problem is provided by the fact that the solid oral form of the antibody-based drug comprises an effective quantity of a carrier, irrigated with the aqueous-alcoholic dilution of antibodies in activated form prepared by combining repeated successive dilution of antibodies with external action and pharmaceutically acceptable additives.

In this case, aqueous-alcoholic dilution contains the activated form of antibodies to endogenous compound participating in regulation or affecting the mechanisms of formation of pathological syndrome, wherein the activated form is prepared by way of repeated dilution and external action using homeopathic technique.

It is possible to use mechanical shaking or ultrasonic or electromagnetic treatment of the dilutions as an external action.

In addition, the drug contains a neutral substance—lactose as a carrier, and a binder and a lubricant as pharmaceutically acceptable additives.

In this case, as pharmaceutically acceptable additives, the solid oral form additionally contains a neutral carrier—lactose in the amount of 30 to 80 wt. % of the mass of the solid oral form—a tablet, and as a binder, it contains microcrystalline cellulose in the amount of 10.0 to 15.0 wt. % of the mass of the solid oral form—a tablet, and as a lubricant, it contains magnesium stearate in the amount of 0.8 to 1.2 wt. % of the mass of the solid oral form—a tablet.

The activated form of antibodies constitutes a mixture of various decimal and/or centesimal aqueous-alcoholic homeopathic dilutions.

The solution of the problem is also achieved by the fact that the method for producing the solid oral form of the antibody-based drug comprises preparation of a aqueous-alcoholic dilution of antibodies in activated form, obtained by combining repeated successive dilutions and external action using homeopathic technique, irrigating of a neutral carrier with this aqueous-alcoholic dilution in a fluidized boiling bed with concurrent drying at the temperature up to 35° C., mixing with pharmaceutically acceptable additives in pharmaceutically acceptable sequence, and subsequent pelletization—tablet formation using direct dry pressing.

In this case, a neutral substance—lactose is used as a carrier with the particle size between 150 and 250 μm.

Introduction of antibodies in activated form to the solid drug formulation according to the proposed technique provides a possibility of oral administration of the antibody-based drug while preserving a biological activity.

Utilization of a mixture of various centesimal alcoholic homeopathic dilutions as activated form of antibodies increases therapeutic efficacy of the proposed drug under condition of individual tolerance (insensibility) of the body with respect to a certain dilution.

Besides, the qualitative, quantitative, granulometric and structural compositions of the proposed ingredients (components) ensure reliable tablet formation using direct dry pressing while utilizing a limited number of additives.

Embodiments of Invention

In order to prepare a pharmaceutical substance, polyclonal antibodies, monoclonal antibodies and natural antibodies to the substance participating in regulation or affecting the mechanisms of pathological syndrome formation are used.

Methods for obtaining antibodies are described, for example, in the source: Immunological methods (in Rus.), edited by G. Frimel, Moscow, "Meditsina", 1987, pp.9-33.

Polyclonal antibodies, specifically binding with compounds of different categories, e.g., proteins, polynucleotides, oligosaccharides, glycolipids, etc., as well as interacting with low molecular weight substances (haptens), are produced as a result of active immunization of animals. For this purpose, animals are given a series of injections according to a specifically developed schedule with antigen, which represents either an individually isolated high-molecular substance, or a synthetic conjugate—in case of using haptens. As a result of conducting such procedure, a monospecific antiserum with high antibody content is obtained for further use. If necessary, purification of antibodies present in antiserum is conducted. For this purpose, fractionation with salt precipitation or ion exchange chromatography are used.

Monoclonal antibodies of various specificity, which interact with low molecular weight haptens as well as with epitopes of high-molecular substances, are obtained using hybridome technique. The initial stage of the process includes immunization based on principles already developed during preparation of polyclonal antiserums. Further stages of work provide for obtaining of hybrid cells producing clones of similar in specificity antibodies. Their individual isolation is done using the same methods as in the case of polyclonal antiserums.

Natural antibodies to exogenous antigens and bioregulators of different nature are isolated from the human blood serum using affinity chromatography. For this purpose, a carrier with covalently bound antigen, which represents either a hapten or a macromolecular compound, is used as immunosorbent. As a result of conducting chromatography, a population of antibodies with narrow distribution in specificity and affinity is obtained, Isolated substance or drug antibodies undergo successive repeated dilution in combination with external action, which is predominantly a vertical shaking, until an activated form is obtained, for example, using homeopathic potentiation technique (see, for example, V. Shvabe, Homeopathic drugs (in Rus.). A description and preparation guide, Moscow, 1967, pp. 12-38; or G. Keller, Homeopathy (in Rus.), Moscow, "Meditsina", 2000, part 1, pp. 37-40). In this case, uniform decrease in concentration is achieved by gradually diluting of I volumetric part of initial substance (antibodies) in 9 volumetric parts (for decimal dilution D) or in 99 volumetric parts (for centesimal dilution C), or in 999 volumetric parts (for millesimal dilution) of a neutral solvent—distilled water and/or 70% ethyl alcohol followed by repeated vertical shaking of each obtained dilution as well as utilization of predominantly separate containers for each subsequent dilution until desired concentration is achieved.

External action in the process of concentration reduction can also be conducted using ultrasound or electromagnetic action, as well as other mechanical action.

During the next stage, in order to produce a pharmaceutical substance—an active substance in the form of "saturated" lactose, irrigating of granules of the neutral substance—lactose (milk-sugar) with the particle size of 150-250 μm, introduced into the fluidized bed, with the activated form of antibodies prepared using a aqueous-alcoholic dilution (preferably, centesimal) with concurrent drying at temperatures up to 35° C. is conducted using a fluidized bed apparatus, e g., "Hiittlin Pilotlab" manufactured by Hiittlin GmbH.

Calculated amount of prepared pharmaceutical substance—active substance in the form of "saturated" lactose—is loaded into a mixer and mixed with microcrystalline cellulose introduced in the amount of 10.0-15.0 wt. % of the total mass of the load. Then, an "unsaturated" lactose is added to the mixture (as required in order to reduce cost and somewhat simplify and speed-up technological process without decline in efficacy of the therapeutic treatment due to reduction in pharmaceutical substance content in the tablet: a aqueous-alcoholic dilution of antibodies in activated form) in the amount of 30-80 wt. % of the total mass of the load, and magnesium stearate in the amount of 0.8-1.2 wt. % of the total mass of the load, followed by uniform mixing.

Obtained dry homogeneous mixture is supplied to the pelletizing machine, for example, tablet-press Korsch—XL 400, to form round 150-500 mg tablets using direct dry pressing.

Described below is an example of producing a drug as an activated form of the polyclonal morphine antibodies (antiserum), the process of which is conducted in several stages.

The stage of producing a morphine-ovalbumin conjugate.

A solution of 50 mg (0.001 mmol) of ovalbumin in 5.0 ml of distilled water is mixed with 2.0 ml of dimethylformamide containing 15.0 mg (0.039 mmol) of morphine 6-hemisuccinate, to which, while cooling down, a solution of 15 mg (0.055 mmol) of water-soluble carbodiamide in 3 ml of distilled water is added drop wise. Reaction mixture is incubated for 5 hours at 4° C. Obtained conjugate is isolated using gel-chromatography on a column with Sephadex G25 and liophilicly dried.

The amount of bound morphine is calculated based on UV-spectra of the initial protein and obtained conjugate using the change in absorption at 280 nm. Based on UF-spectra data, synthesized conjugate contains 12-15 moles of hapten per one mole of protein.

The stage of producing morphine-ovalbumin conjugate monospecific serum.

Immunization of "Vienna blue" rabbits weighing no more than 2 kg is conducted on the cycling basis with 10-day interval. The maximum number of injection is 4. Conjugate is administered to the front and rear extremities in the area of articular lymph nodes in the amount of 1 mg per immunization. For this purpose, the antigen is preliminary dissolved in 1 ml of complete Freund's adjuvant. The volume of immunization mixture is 2 ml. Further immunizations are done using incomplete Freund's adjuvant while maintaining above-specified proportions of antigen and adjuvant. Trial blood sample is taken from the animal's peripheral ear vein 10 days after immunization.

Rabbit blood serum is obtained by centrifuging at 1000 g for 10 minutes at room temperature followed by adding chloroform as a preservative until a final concentration of 13% is reached.

Obtained antiserum is checked using immune-enzyme analysis for presence of morphine-specific antibodies, which are determined using enzyme-marked antispecies antibody conjugate.

So obtained antiserum contains specific antibodies in dilution of 1:1000-1:25000.

Next, a γ-globulin-rich fraction is isolated from the produced antiserum. For this purpose, protein precipitation with 50% ammonium sulfate is used followed by washing the residue with 30% saline solution, centrifuging and conducting dialysis against phosphate buffer. So prepared fraction, containing given antigen-specific antibodies, is used during the next stage to prepare the drug.

The stage of producing an activated form of morphine antibodies.

0.5 ml of γ-globulin fraction of antiserum are placed into a $E-6_1$ container, followed by adding 4.5 ml of distilled water and shaking 10 times, which results in 5 ml of the $1^{st}$ centesimal dilution. Then, 0.05 ml of the $1^{st}$ centesimal dilution are placed into E-62 container, followed by adding 4.95 ml of distilled water and shaking 10 times, which results in 5.0 ml of the $2^{nd}$ centesimal dilution. The $3^{rd}$ through the $29^{th}$ centesimal dilutions are prepared similar to the $2^{nd}$ centesimal dilution.

The final $30^{th}$ centesimal dilution is obtained by diluting the $29^{th}$ dilution in 70% ethyl alcohol.

Obtained aqueous-alcoholic solution is used for irrigating in a fluidized bed the particles of a neutral carrier—lactose (milk-sugar) when producing a pharmaceutical substance of active compound in the form of "saturated" lactose, which serves as a basis for direct dry press-forming of the solid oral form (round tablets with the mass predominantly 240 and 300 mg) of the proposed drug.

Provided below are the examples of treating various pathological syndromes using a solid form of the drug based on activated form of antibodies, which are conditionally (based on similarity with the terminology used in homeopathic literature) called potentiated antibodies.

EXAMPLE 1

Patient V., 19 years old. Administers himself with heroin by inhalation at least 3 times a week for 2 months. Based on parental consent, the patient was hospitalized and placed in isolated unit for 24 days. 2 days after admission the patient became irritable and developed sleep disturbance. During conversation, mentioned that he noticed attraction to narcotics. Prescribed: 1 tablet "saturated" with potentiated antibodies—homeopathic dilution C30 of the γ-globulin fraction of antiserum to morphine hydrochloride—6 times a day. 3 weeks later the patient demonstrated steady mood, satisfactory appetite and sleep. During individual session with psychologist, the patient stated that he experienced no attraction. Recommended to continue taking heroin antibodies on a daily basis at 1 tablet a day. 2 months after discharging from the hospital, according to his mother, the patient does not take any narcotics.

EXAMPLE 2

Patient K., 57 years old, suffering from rheumatoid arthritis (RA) for 5 years, class III according to functional classification of the American College of Rheumatology, and was hospitalized due to exacerbation of the disease. Upon admission: complaints about fever, considerable increase in morning stiffness and pain in affected joints, their inflammation, Objectively: temperature 37.5° C., pronounced hyperemia and defiguration of wrist, ankle and proximal interphalangeal joints, pain during palpation. In blood test: ESR 35 mm/h, rheumatoid factor++. Due to poor tolerance of non-steroid anti-inflammatory drugs, prescribed: 1 tablet "saturated" with potentiated antibodies—a mixture of homeopathic dilutions C50, C200 (1:1) of monoclonal antibodies to recombinant human tumor necrosis factor alpha—3 times a day. 3 days after the beginning of treatment, the patient observed considerable reduction in pain syndrome, body temperature dropped to normothermia. On the $7^{th}$ day of treatment: morning stiffness observed before hospitalization still remains. The patient was discharged on the $14^{th}$ day with the clinical-laboratory remission. Recommended prophylactic administration of the drug by taking 1 tablet every other day. 2 months after discharge, the patient's class is changed from III to II according to RA functional classification.

EXAMPLE 3

Patient S., 51 years old, came to see urologist with complains about decrease in libido, erection abnormality, lower satisfaction from sexual intercourse. Mentioned symptoms intensified over the past 2 years. During the last 3 years also observed occasional depression, grizzle, memory impairment and sleep disturbance, decrease in ability to work, palpitation attacks, fluctuations in arterial blood pressure. Objectively: revealed moderate enlargement of prostate gland. Diagnosis: erectile dysfunction with involutional hormonal changes. Prescribed: 1 tablet "saturated" with potentiated antibodies—a mixture of homeopathic dilutions of monoclonal antibodies to a fragment of human endothelium NO synthase D6, C30 and C200 (1:1:1)—once every 3 days. 2 weeks after the beginning of treatment, the patient demonstrated improvement in erection and increase in libido along with general improvement in health condition: higher overall tonus, better sleep. Recommended taking medicine 1-2 times a week. During follow-up visit 2 months after the beginning of treatment, the patient expressed no previous complaints, observed recovery in libido level, erection and satisfaction from the intercourse.

What is claimed is:

1. A method for producing a solid oral dosage form of an antibody-based medicinal preparation, said method comprising:
   a. providing at least one antibody in a molecular form,
   b. carrying out multiple consecutive dilution of at least one antibody in accordance with homeopathic technique resulting in a homeopathic dilution;
   c. providing a solid neutral carrier;
   d. irrigating said solid neutral carrier with said homeopathic dilution in a fluidized boiling bed with concurrent drying at a temperature equal to or less than 35° C.; and
   e. forming said solid neutral carrier into said solid oral dosage form.

2. The method according to claim 1, wherein said neutral carrier is lactose.

3. The method of claim 2, wherein said lactose has particle size ranging from 150 to 250 μm.

4. The method of claim 1, wherein said oral dosage form is a tablet prepared by direct dry compression.

* * * * *